UnitedStates Patent [19]

Chiba et al.

[11] Patent Number: 4,764,528

[45] Date of Patent: Aug. 16, 1988

[54] 2,4-PENTADIENOIC ACID DERIVATIVES AND PLATELET AGGREGATION INHIBITORS CONTAINING THE SAME

[75] Inventors: Keiko Chiba, Tsuchiura; Makoto Takai, Hachioji; Toshio Wakabayashi, Tama, all of Japan

[73] Assignee: Terumo Kabushiki Kaisha t/a Terumo Corporation, Tokyo, Japan

[21] Appl. No.: 26,993

[22] Filed: Mar. 10, 1987

[30] Foreign Application Priority Data

Mar. 17, 1986 [JP] Japan ................................. 61-57084

[51] Int. Cl.$^4$ ..................... C07C 59/46; A61K 31/19
[52] U.S. Cl. .............................. 514/510; 260/410.5; 260/410.9 R; 260/413; 260/501.1; 560/116; 560/119; 562/498; 562/501
[58] Field of Search ............... 560/116, 119; 562/498, 562/500, 501; 514/510, 559, 573; 260/410 R, 413 L, 501.1, 410.5, 410.9 R, 410.9 Q, 410.9 P

[56] References Cited

U.S. PATENT DOCUMENTS 4,588,823  5/1986  Aristoff .......................... 562/501 X

FOREIGN PATENT DOCUMENTS 0150039  11/1981  Japan ................................. 514/510
0089443   5/1985  Japan ................................. 560/119
0202840  10/1985  Japan ................................. 560/119
84/02902  8/1984  World Int. Prop. O. .......... 562/501

Primary Examiner—Michael L. Shippen
Attorney, Agent, or Firm—Burns, Doane, Swecker & Mathis

[57] ABSTRACT

Novel 2,4-pentadienoic acid derivatives are disclosed. As the examples are mentioned 3-(4-carboxy-trans, trans-1,3-butadienyl)-6-exo-(3α-hydroxy-trans-1-octenyl)-7-endo-hydroxybicyclo[3.3.0]oct-2-ene, 3-(5-carboxy-trans, trans-2,4-pentadienyl)-6-exo-(3α-hydroxytrans-1-octenyl)-7-endo-hydroxybicyclo[3.3.-0]oct-2-ene and the like. These compounds are useful as a platelet aggregation inhibitor, especially as a thrombosis-prophylactic agent.

5 Claims, No Drawings

2,4-PENTADIENOIC ACID DERIVATIVES AND PLATELET AGGREGATION INHIBITORS CONTAINING THE SAME

BACKGROUND OF THE INVENTION (1) Field of the Invention

The present invention relates to novel 2,4-pentadienoic acid derivatives and platelet aggregation inhibitors containing the same. The 2,4-pentadienoic acid derivatives provided by the invention are novel compounds which possess a potent antiplatelet activity. Accordingly, they are useful in preventing diseases caused by platelet aggregation, that is diseases such as thrombosis.

(2) Description of Prior Arts

A variety of compounds are known to have antiplatelet activities. However, the prior art compounds such as, for example, prostaglandin $I_2$ ($PGI_2$) contain unstable vinylether group in the molecule so that the half life in the living body is short. Carbacyclins in which the 6,9-oxygen atoms in the molecule are replaced by carbon atoms to improve the above problem are also known. Nevertheless, there are no practically effective therapeutic agents, and development of more improved drugs is desirable. Recently, thromboses such as myocardial infarction and cerebral thrombosis have been a greater part of adult diseases and development of antithrombic agents capable of effectively preventing such diseases is also strongly desired.

SUMMARY OF THE INVENTION

As a result of extensive studies on the syntheses and pharmacological activities of 2,4-pentadienoic acid derivatives, we have found that specific 2,4-pentadienoic acid derivatives possess high platelet aggregation-inhibiting activities.

Accordingly, it is an object of this invention to provide a 2,4-pentadienoic acid derivative represented by the general formula (I)

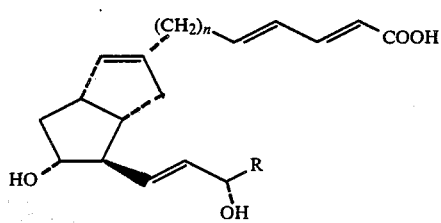

wherein R is a group having the formula

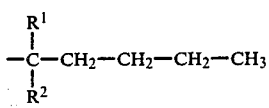

in which $R^1$ and $R^2$ may be the same or different and each represents a hydrogen atom or a lower alkyl group, a group having the formula

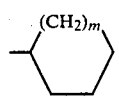

in which m represents 1 or 2 or a group having the formula

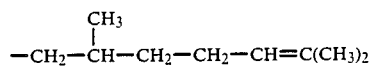

and n represents an integer from 0 to 3 and an ester or a pharmacologically acceptable salt thereof.

A further object of the invention is to provide a platelet aggregation inhibitor comprising a 2,4-pentadienoic acid derivative having the above-mentioned formula (I) or an ester or a pharmacologically acceptable salt thereof.

DETAILED DESCRIPTION OF THE INVENTION

According to the present invention, there are provided a novel 2,4-pentadienoic acid derivative represented by the above-mentioned formula (I) and an ester or a pharmacologically acceptable salt thereof.

In the definition of the substituents in the formula (I) the lower alkyl group means a straight or branched alkyl group containing from 1 to 4 carbon atoms and is preferably a methyl or ethyl group.

As esters of the 2,4-pentadienoic acid derivatives having the formula (I) are mentioned lower alkyl esters, for example, a methyl, ethyl or n-butyl ester, lower alkoxymethyl esters, for example, a methoxymethyl or ethoxymethyl ester, lower aliphatic acyloxymethyl esters, for example, an acetoxymethyl or propionyloxymethyl ester or a benzyl ester of said carboxylic acid. As the pharmacologically acceptable salts are mentioned alkali metal salts, for example, a sodium, potassium or lithium salt or ammonium salts, for example, an ammonium, cyclohexylammonium or diisopropylammonium salt of said carboxylic acid.

These esters or salts can easily be produced by esterifying the 2,4-pentadienoic acid derivatives (I) according to a conventional method or reacting the compounds (I) with a corresponding base (for example, a caustic alkali).

Depending upon the number of the n in the formula, the 2,4-pentadienoic acid derivatives (I) are prepared as follows:

The 2,4-pentadienoic acid derivative of the general formula (I) wherein n is 0, i.e., a 2,4-pentadienoic acid derivative represented by the general formula

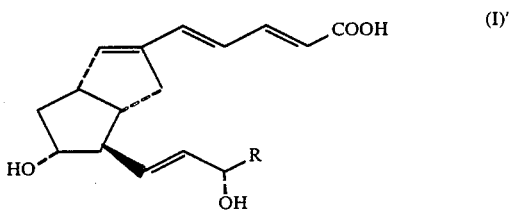

wherein R has the same meaning as defined above can be prepared by condensing an aldehyde derivative represented by the fornula (II)

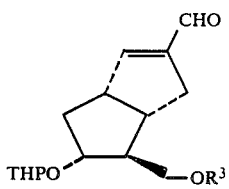

wherein THP denotes a tetrahydropyranyl group and R³ represents a t-butyldimethylsilyl group with trialkyl (e.g. ethyl)-4-phosphonocrotonate to give a 2,4-pentadienoic acid derivative represented by the formula (III)

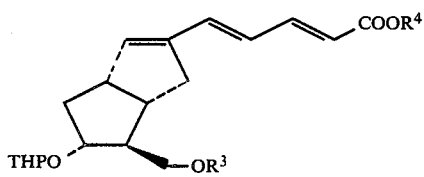

wherein THP and R³ have the same meanings as defined above and R⁴ represents an alkyl group (e.g. ethyl group), eliminating the group R³ in the product followed by oxidation to give a 2,4-pentadienoic acid aldehyde derivative represented by the formula (IV)

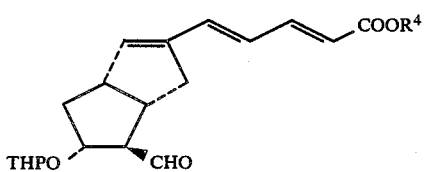

wherein THP and R⁴ have the same meaning as defined above, reacting the product with a phosphonate represented by the formula (V)

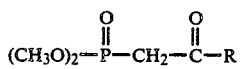

wherein R has the same meaning as defined above to give a 2,4-pentadiene ketone derivative represented by the formula (VI)

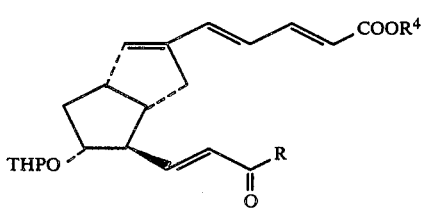

wherein THP and R have the same meanings as defined above, and reducing the product with sodium borohydride or Selectride, a trademark for tri-sec-butylborohydride, followed by elimination of the protective group (THP).

The 2,4-pentadienoic acid derivative wherein n in the above-mentioned formula (I) is an integer from 1 to 3, i.e., a 2,4-pentadienoic acid derivative represented by the general formula (I)″

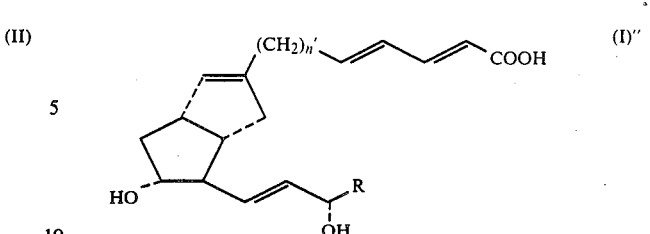

wherein R has the same meaning as defined above and n' represents an integer from 1 to 3 are prepared by reacting an aldehyde derivative represented by the above-mentioned formula (II) with methyltriphenylphosphonium bromide to give a vinyl derivative represented by the formula (VII)

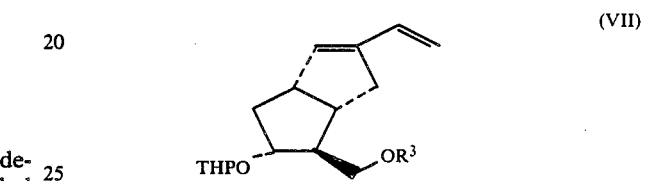

wherein THP and R³ have the same meanings as defined above, hydroboronating the product with disiamylborane followed by oxidation to give an alcohol derivative represented by the formula (VIII)

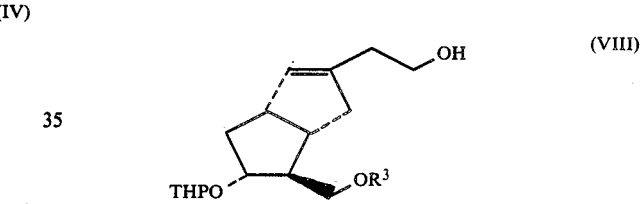

wherein THP and R³ have the same meanings as defined above, oxidizing the product to give an aldehyde derivative represented by the formula (IX)

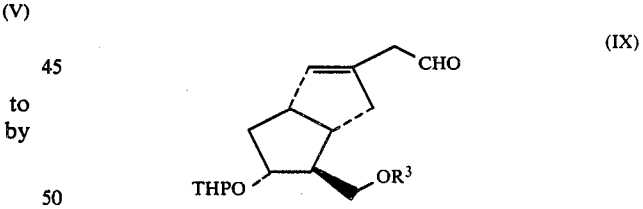

wherein THP and R³ have the same meanings as defined above, which has one more methylene group than in the above compound (II) subsequently repeating (n'-2) times the reaction with methyltriphenylphosphonium bromide to give an alcohol derivative represented by the formula (X)

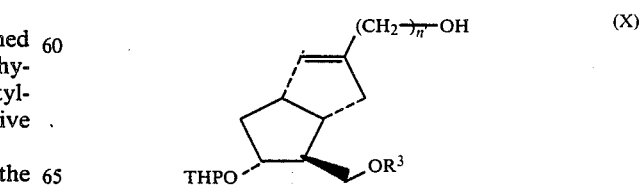

wherein THP and n' have the same meanings as defined above, subjecting the product to acylation (e.g. acetylation), elimination of the protective group R³ and then oxidation to give an aldehyde derivative represented by the formula (XI)

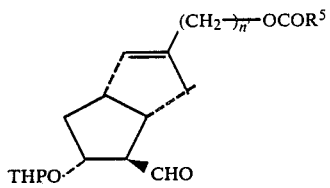

(XI)

wherein THP and n' have the same meanings as defined above and R⁵ represents an alkyl group (e.g. methyl group), reacting the product with a phosphonate represented by the above-mentioned formula (V) to give a ketone derivative represented by the formula (XII)

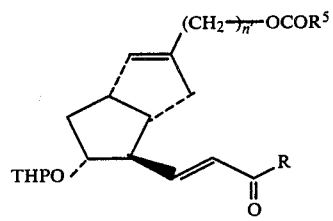

(XII)

wherein THP, R, n' and R⁵ have the same meanings as defined above, reducing the product with a reducing agent such as sodium borohydride or Selectride, protecting the hydroxyl group in the product with a tetrahydropyranyl group, eliminating the acyl (e.g. acetyl) group with methanol and potassium carbonate and then subjecting the product to oxidation to given an aldehyde derivative represented by the formula (XIII)

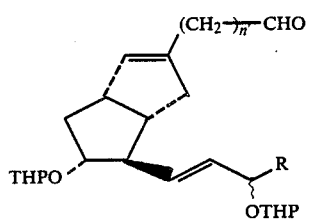

(XIII)

wherein THP, R and n' have the same meanings as defined above, reacting the product with trialkyl (e.g. ethyl)-4-phosphonocrotonate to give a 2,4-pentadienoic acid derivative represented by the formula (XIV)

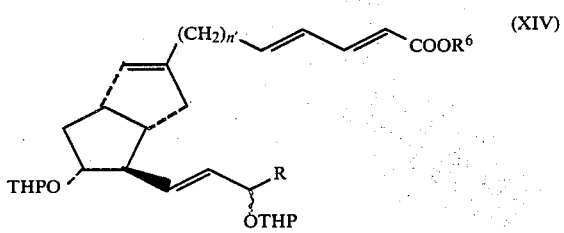

(XIV)

wherein THP, R and n' have the same meanings as defined above and R⁶ represents an alkyl group (e.g. ethyl group) and subjecting the product to elimination of the protective groups.

The 2,4-pentadienoic acid derivatives of the invention represented by the above-mentioned formula (I) can be used in the platelet aggregation-inhibiting agent as the active ingredient or one of the active ingredients. Any disease caused by platelet aggregation is effectively treated, and particularly they are useful as therapeutic agents for arterial thrombosis of extremities and cerebral thrombosis and also as prophylactic agents. The dosage which may depend upon the route of administration is generally in the range between 5 μg and 500 μg per day in human adults which may preferably be divided into 1-3 doses as required. The administration may be in any form, but oral administration is desirable. Intravenous injection is also feasible.

The compounds of the invention are blended by conventional procedures with pharmaceutical carriers or excipients, and the blends are formed into tablets, powders, capsules or granules. As examples of the carrier or excipient are mentioned calcium carbonate, calcium phosphate, starch, sucrose, lactose, talc, magnesium stearate and the like. In addition to solid preparations as above, the compounds of the invention can also be formed into liquid preparations such as fat emulsion or syrup or injectable preparations.

The compounds of the invention can also be stabilized by inclusion with cyclodextrin.

Typical examples and test examples will be given below to describe the invention in more details. It is, however, to be understood that the invention is no way limited to these examples.

EXAMPLE 1

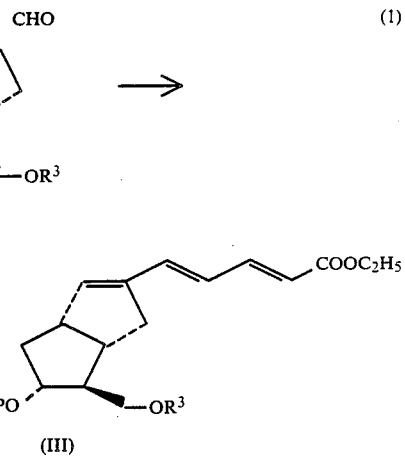

In 2.5 ml of THF (tetrahydrofuran) was suspended sodium hydride (60% in oil, 120 mg, 3 mmol) washed with n-hexane. To the suspension was added triethyl-4-phosphonocrotonate (750 mg, 3 mmol). The mixture was stirred at room temperature for 10 min., followed by addition of a THF solution of 1-3-formyl-6-exo-t-butylsilyloxymethyl-7-endo-tetrahydropyranyloxybicyclo[3.3.0]oct-2-ene (II) (620 mg, 1.56 mmol). The mixture was stirred at room temperature for 1 hour, followed by addition of a saturated aqueous solution of ammonium chloride, removal of the THF by distillation under reduced pressure and then extraction with ethyl acetate. The organic layer was washed with a saturated aqueous solution of sodium chloride. The layer was then dried over sodium sulfate, and the solvent was removed by distillation. The residue thus obtained was purified by column chromatography on silica gel (hexane:ether=9:1) to give 1-3-(4-ethoxycarbonyl-trans, trans-1,3-butadienyl)-6-exo-t-butyldimethylsilyloxymethyl-7-endo-tetrahydropyranyloxybicyclo[3.3.-0]oct-2-ene (III) 390 mg, 50%).

IR (CHCl$_3$) cm$^{-1}$: 2950, 2875, 1702, 1618.

PMR (CDCl$_3$) δ: 0.08(s, 6H), 0.92(s, 9H), 1.27(t, 3H, J=7 Hz), 4.18(q, 2H, J=7 Hz), 4.60(bs, 1H), 5.80(d, 1H, J=16 Hz), 5.86(bs, 1H), 6.08(dd, 1H, J=16.11 Hz), 6.71(d, 1H, J=16 Hz), 7.28(dd, 1H, J=16.11 Hz).

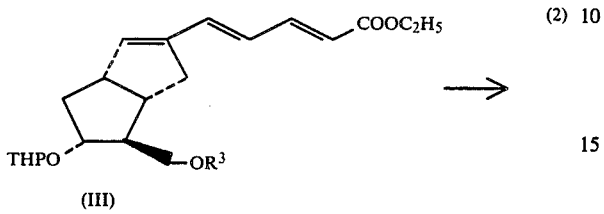

Said 2,4-pentadienoic acid derivative (III) (300 mg, 0.6 mmol) was dissolved in THF (2 ml). To the mixture was added tetra-n-butylammonium flurodide (1M THF solution, 2 ml, 2 mmol). The mixture was stirred at room temperature for 3 hours, followed by addition of saturated aqueous sodium chloride and removal of the THF by distillation under reduced pressure. The residual aqueous layer was extracted with ether, the extract was dried over sodium sulfate and then removal of the solvent by distillation. The residue was purified by column chromatography on silica gel (hexane:ether=1:1) to give 1-3-(4-ethoxycarbonyl-trans, trans-1,3-butadienyl)-6-exo-hydroxymethyl-7-endo-tetrahydropyranyloxybicyclo[3.3.0]oct-2-ene (XV) (186 mg, 85%).

IR (CHCl$_3$) cm$^{-1}$: 3625, 3520, 2950, 2875, 1702, 1618.

PMR (CDCl$_3$) δ: 1.27(t, 3H, J=7 Hz), 4.17(q, 2H, J=7 Hz), 4.65(bs, 1H), 5.81(d, 1H, J=16 Hz), 5.87(bs, 1H), 6.10 (dd, 1H, J=16.11 Hz), 6.70(d, 1H, J=≠Hz), 7.28(dd, 1H, J=16.11 Hz).

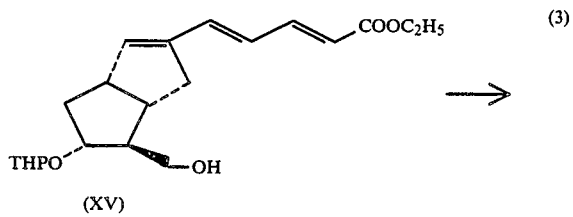

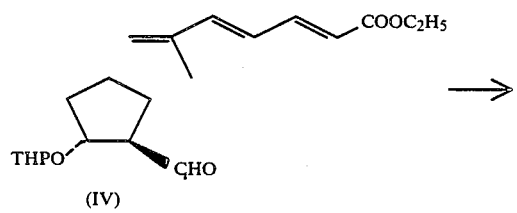

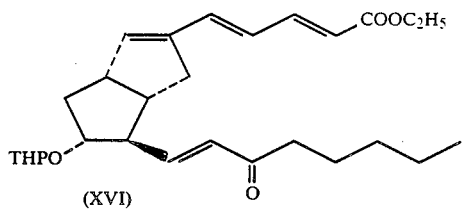

Collins reagent (CrO$_3$.2Py, 1.29 g, 5 mmol) and Celite, a trademark of a filter aid made of SiO$_2$ powder by Johns Manville Corporation, (1.3 g) were suspended in the atmosphere of argon in methylene chloride (20 ml). To the suspension was added a methylene chloride solution (5 ml) of 1-3-(4-ethoxycarbonyl-trans, trans-1,3-butadienyl)-6-exo-hydroxymethyl-7-endo-tetrahydropyranyloxybicyclo[3.3.0]oct-2-ene (XV) (93 mg, 0.25 mmol). The mixture was stirred at 0° C. for 30 min., followed by addition of sodium hydrogen sulfate monohydrate (2.56 g) and stirring at 0° C. for additional 10 min. The reaction mixture was filtered with the aid of sodium sulfate and washed with methylene chloride. From the combined filtrate was removed the solvent by distillation to give 3-(4-ethoxycarbonyl-1,3-butadienyl)-6-exo-formyl-7-endo-tetrahydropyranyloxybicyclo[3.3.0]oct-2-ene (IV).

Separately, sodium hydride (60% in oil, 20 mg, 0.5 mmol) was washed with n-hexane and suspended in 5 ml of DME (dimethoxyethane). To the suspension was added a DME solution (5 ml) of dimethyl (2-oxoheptyl)phosphonate (111 mg, 0.5 mmol), and the mixture was stirred at room temperature for 25 min. To the resulting mixture was added a DME solution (5 ml) of the 3-(4-ethoxycarbonyl-trans, trans-1,3-butandienyl)-6-exo-formyl-7-endo-tetrahydropyranyloxybicyclo[3.3.-0]oct-2-ene obtained above. The mixture was stirred at room temperature for 1 hour, followed by addition of saturated aqueous solution of ammonium chloride, removal of the DME by distillation under reduced pressure and then extraction with ether. The ether layer was washed with saturated aqueous sodium chloride and dried over anhydrous sodium sulfate. The solvent was then removed by distillation, and the residue thus obtained was purified by column chromatography on silica gel (hexane:ether=1:1) to give 3-(4-ethoxycarbonyl-trans, trans-1,3-butadienyl)-6-exo-(3-oxo-trans-1-octenyl)-7-endo-tetrahydropyranyloxybicyclo[3.3.-0]oct-2-ene (XVI) (67 mg, 57%).

IR(CHCl$_3$)cm$^{-1}$: 2940, 2880, 1702, 1665, 1620.

PMR(CDCl$_3$) δ: 0.88(t, 3H, J=5 Hz), 1.28(t, 3H, J=7 Hz), 4.18(q, 2H, J=7 Hz), 4.57(bs, 1H), 5.83 (d, 1H, J=16 Hz), 5.85(bs, 1H), 6.12(dd, 1H, J=16.2 Hz), 6.70 (d, 1H, J=16 Hz), 6.80(m, 1H), 7.28(dd, 1H, J=16.11 Hz).

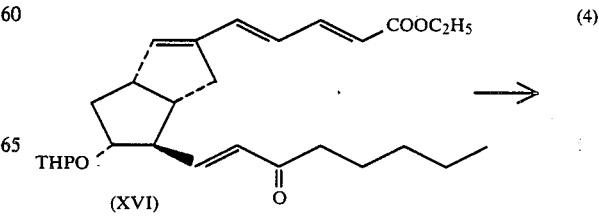

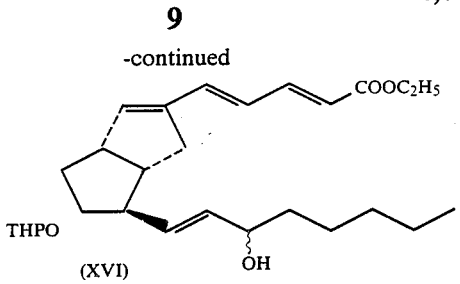
(XVI)

3-(4-Ethoxycarbonyl-trans, trans-1,3-butadienyl)-6-exo-(3-oxo-trans-1-octenyl)-7-endo-tetrahydropyranyloxybicyclo[3.3.0]oct-2-ene (XVI) (67 mg, 0.14 mmol) was dissolved in methanol (10 ml). To the solution cooled in −20° C. was added sodium borohydride (27 mg, 0.71 mmol). The mixture was stirred at −20° C. for 20 min., followed by addition of an excess of acetone, warming to room temperature, addition of saturated aqueous solution of ammonium chloride and then removal of the methanol and acetone by distillation under reduced pressure. The residual aqueous layer was extracted with ether, the extract was dried over anhydrous sodium sulfate and the solvent was removed by distillation to give 3-(4-ethoxycarbonyl-trans, trans-1,3-butadienyl)-6-exo-(3-hydroxy-trans-1-octenyl)-7-endo-tetrahydropyranyloxybicyclo[3.3.0]oct-2-ene (XVII) (68 mg, 100%).

IR(CHCl$_3$)cm$^{-1}$: 3620, 3400, 2940, 2870, 1702, 1619.

PMR(CDCl$_3$) δ: 0.88(t, 3H, J=5 Hz), 4.61(bs, 1H), 5.53(m, 2H), 5.78(d, 1H, J=16 Hz), 5.82(bs, 1H), 6.05(dd, 1H, J=16.11 Hz), 6.65(d, 1H, J=16 Hz), 7.20(dd, 1H, J=16.11 Hz).

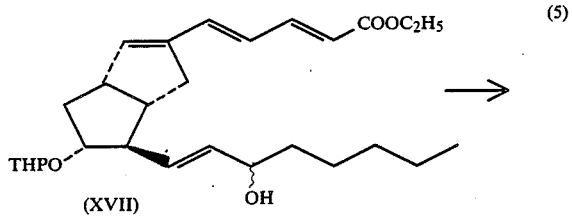
(XVII)

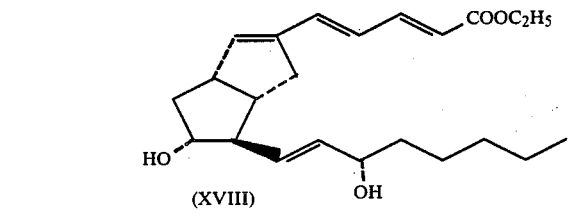
(XVIII)
+
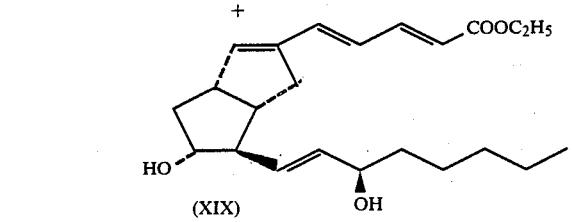
(XIX)

A solution of 3-(4-ethoxycarbonyl-trans, trans-1,3-butadienyl)-6-exo-(3-hydroxy-trans-1-octenyl)-7-endo-tetrahydropyranyloxybicyclo[3.3.0]oct-2-ene (XVII) (68 mg, 0.14 mmol) in a mixture of acetic acid:water:THF (1 ml) (3:1:1: by volume) was stirred at 45°–50° C. for 3 hours. The resulting solution was diluted with ether and then neutralized with saturated aqueous sodium bicarbonate. The ether layer was washed with saturated aqueous sodium chloride and dried over anhydrous sodium sulfate. The solvent was removed, and the residue was purified by column chromatography on silica gel (ether:n-hexane=5:1 −ether:methanol=40:1). There were obtained 3-(4-ethoxycarbonyl-trans, trans-1,3-butadienyl)-6-exo-(3α-hydroxy-trans-1-octenyl)-7-endo-hydroxybicyclo[3.3.0]oct-2-ene (XVIII) (30 mg, 57%) as a more polar fraction and 3-(4-ethoxycarbonyl-trans, trans-1,3-butadienyl)-6-exo-(3β-hydroxy-trans-1-octenyl)-7-endo-hydroxybicyclo[3.3.0]oct-2-ene (XIX) (16 mg, 28%) as a less polar fraction.

Spectrum data of (XVIII)

IR(CHCl$_3$)cm$^{-1}$: 3610, 3400, 2970, 2940, 2860, 1700, 1618.

PMR(CDCl$_3$) δ: 0.88(t, 3H, J=5 Hz), 1.28(t, 3H, J=7 Hz), 4 20(q, 2H, J=7 Hz), 5.53(m, 2H), 5.83(d, 1H, J=16 Hz), 5.87(bs, 1H), 6.10(dd, 1H, J=16.11 Hz), 6.73(d, 1H, J=16 Hz), 7.30(dd, 1H, J=16.11 Hz).

Spectrum data of (XIX)

IR(CHCl$_3$)cm$^{-1}$: 3610, 3400, 2970, 2940, 2860, 1700, 1618.

PMR(CDCl$_3$) δ: 0.88(t, 3H, J=5 Hz), 1.28(t, 3H, J=7 Hz), 4.20(q, 2H, J=7 Hz), 5.60(m, 2H), 5.83(d, 1H, J=16 Hz), 5.85(bs, 1H), 6.11(dd, 1H, J=16.11 Hz), 6.70(d, 1H, J=16 Hz), 7.28(dd, 1H, J=16.11 Hz).

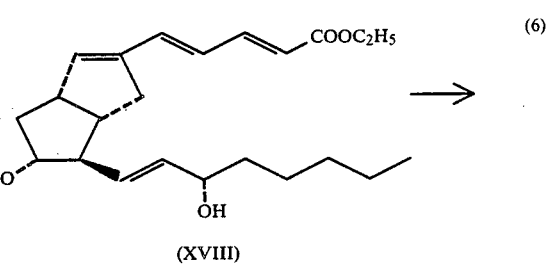
(XVIII)

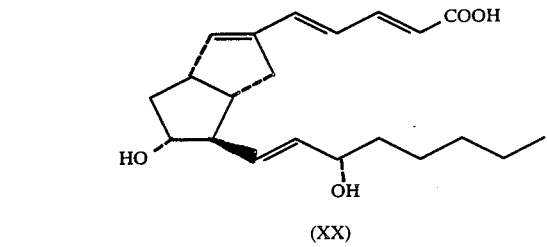
(XX)

To a solution of 3-(4-ethoxycarbonyl)-trans, trans-1,3-butadienyl)-6-exo-(3α-hydroxy-trans-1-octenyl)-7-endo-hydroxybicyclo[3.3.0]oct-2-ene (XVIII) (30 mg, 0.08 mmol) in methanol (0.6 ml) at 0° C. was added 10% aqueous solution of sodium hydroxide (0.4 ml). The mixture was stirred at 0° C. for 9 hours and then neutralized under cooling with 10% aqueous solution of hydrochloric acid. The methanol was removed by distillation under reduced pressure, and then the solvent was removed by distillation to give 3-(4-carboxy-trans, trans-1,3-butadienyl)-6-exo-(3α-hydroxy-trans-1-octenyl)-7-endo-hydroxybicyclo[3.3.0]oct-2-ene (XX) (28 mg, 100%).

IR(KBr)cm$^{-1}$: 3400, 2970, 2940, 2860 1690, 1615.

PMR(d$_6$-acetone)δ: 0.87(t, 3H, J=5 Hz), 5.52(m, 2H), 5.83(d, 1H, J=16 Hz), 5.88(bs, 1H), 6.18(dd, 1H, J=16.11 Hz), 6.80(d, 1H, J=16 Hz), 7.22(dd, 1H, J=16.11 Hz).

The 3β-epimer was also hydrolyzed in the same way as above.

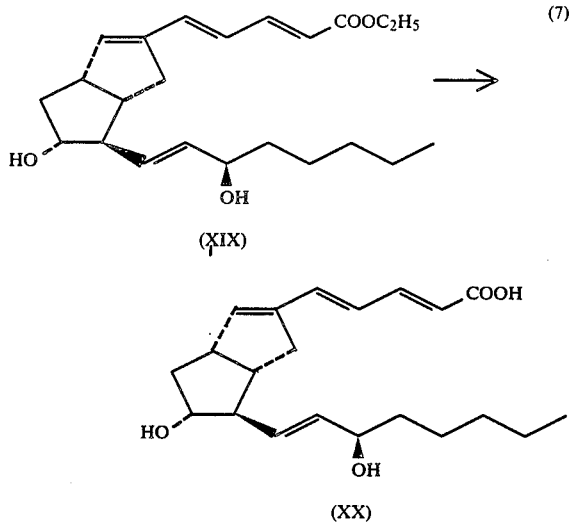

IR(KBr)cm$^{-1}$: 3400, 2970, 2940, 2860, 1690, 1615.
PMR(d$_6$-acetone)δ: 0.87(t, 3H, J=5 Hz), 5.52(m, 2H), 5.85(d, 1H, J=16 Hz), 5.88(bs, 1H), 6.22(dd, 1H, J=16,11 Hz), 6.82(d, 1H, J=16 Hz), 7.25(dd, 1H, J=16,11 Hz).

EXAMPLES 2–5

Condensation reactions with a variety of dimethyl (2-oxoalkyl)phosphonate, reductions with sodium borohydride and deprotection reactions run in the same way as in Example 1 yielded 2,4-pentadienoic acid derivatives shown in Table 1. In every case, the more polar isomer was designated as α-epimer and the less polar isomer as β-epimer. Spectrum data are shown in Table 2.

TABLE 1

| Ex. No. | Starting phosphonate | R in the product (I) |
|---|---|---|
| 2 | (MeO)$_2$−P(=O)−CH$_2$−C(=O)−CH(CH$_3$)−(CH$_2$)$_3$CH$_3$ | (sec-alkyl) |
| 3 | (MeO)$_2$−P(=O)−CH$_2$−C(=O)−C(CH$_3$)$_2$−(CH$_2$)$_3$CH$_3$ | (t-alkyl) |
| 4 | (MeO)$_2$−P(=O)−CH$_2$−C(=O)−CH(CH$_2$CH$_2$/CH$_2$CH$_2$) | (cyclopentyl) |
| 5 | (MeO)$_2$−P(=O)−CH$_2$−C(=O)−CH$_2$−CH(CH$_3$)−CH$_2$−CH$_2$−CH=C(CH$_3$)$_2$ | (citronellyl) |

TABLE 2

| Ex. No. | R in the product (I) | IR(cm$^{-1}$) $\nu_{OH}$ | $\nu_{C=O}$ | $\nu_{C=C}$ |
|---|---|---|---|---|
| 2 |  | 3400 | 1690 | 1615 |
| 3 |  | 3400 | 1690 | 1618 |
| 4 |  | 3400 | 1690 | 1615 |
| 5 |  | 3400 | 1690 | 1617 |

EXAMPLE 6

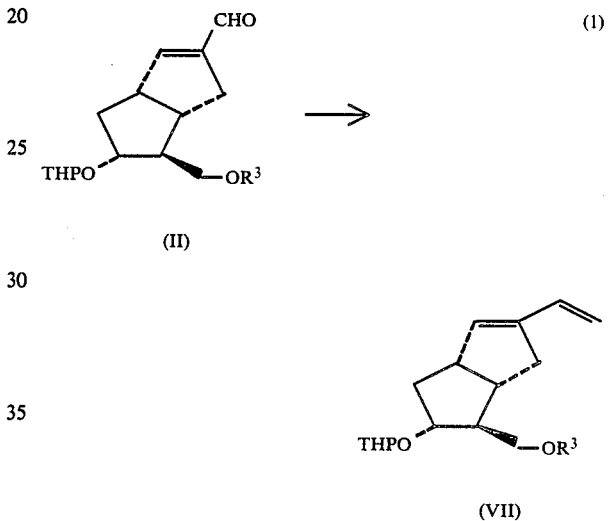

Potassium T-butoxide (672 mg, 6 mmol) was dissolved in an atmosphere of argon in THF (tetrahydrofuran) (10 ml) and to the solution was added methyltriphenylphosphonium bromide (2.1 g, 6 mmol). The mixture was stirred at room temperature for 10 min., followed by addition of a THF solution (5 ml) of 1-3-formyl-6-exo-t-butyldimethylsilyloxymethyl-7-endo-tetrahydropyranyloxybicyclo[3.3.0]oct-2-ene (II) (760 mg, 2 mmol). The mixture was stirred at room temperature for 1 hour, followed by addition of a saturated aqueous solution of ammonium chloride, removal of the THF by distillation under reduced pressure and extraction with ether. The organic layer was washed with a saturated aqueous solution of sodium chloride and dried over sodium sulfate. The solvent was removed by distillation, and the residue thus obtained was purified by column chromatography on silica gel (hexane:ethyl acetate=20:1) to give 3-vinyl-6-exo-t-butyldimethylsilyloxymethyl-7-endo-tetrahydropyranyloxybicyclo[3.3.0]oct-2-ene (VII) (720 mg, 95%).

PMR(CDCl$_3$) δ: 0.07(s, 6H), 0.92(s, 9H), 4.63(m, 1H), 4.88(bs, 1H), 5.10(m, 1H), 5.62(bs, 1H), 6.50(dd, J=9,16 Hz).

IR$\gamma_{max}^{CHCl_3}$ (cm$^{-1}$): 2950, 2870, 1639, 835.

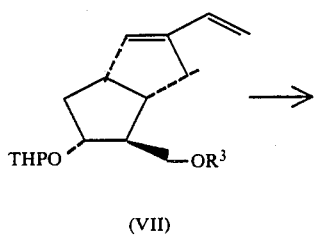

(VII)

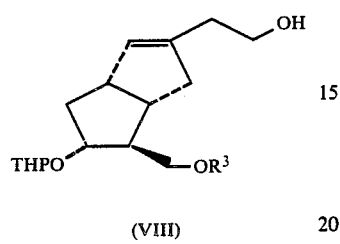

(VIII)

A solution of said vinyl derivative (VII) (720 mg, 1.9 mmol) in 5 ml of THF was added to 40 ml of 0.5M THF solution of disiamylborane at 0° C. The mixture was stirred in an atmosphere of argon at 0° C. for 2 hours, followed by addition of a 6N aqueous solution of sodium hydroxide (13 5 ml) and 30% aqueous hydrogen peroxide (11.5 ml) at 0° C. The mixture was stirred at room temperature for 1.5 hours. The reaction mixture was concentrated under reduced pressure and then extracted with ethyl acetate. The organic layer was washed with an aqueous solution of sodium thiosulfate and a saturated aqueous sodium chloride and dried over sodium sulfate The solvent was then removed by distillation, and the residue was purified by column chromatography on silica gel (hexane-ether=2:1) to give 3-hydroxyethyl-6-exo-t-butyldimethylsilyloxymethyl-7-endo-tetrahydropyranyloxybicyclo[3.3.0]oct-2-ene (VIII) (657 mg, 87%).

PMR(CDCl$_3$) δ: 0.07(s, 3H), 0.92(s, 9H), 3.2–4.2(m, 7H), 4.60(bs, 1H), 5.37(bs, 1H).

IRγ$_{max}^{CHCl_3}$ (cm$^{-1}$): 3620, 3490, 2950, 2850, 835.

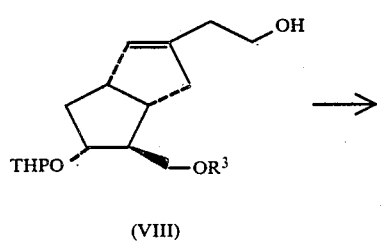

(VIII)

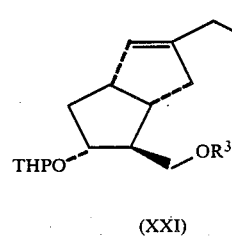

(XXI)

To a solution of said alcohol product (VIII) (567 mg, 1.67 mmol) in 2 ml of pyridine was added 1 ml of acetic achydride, and the mixture was stirred at room temperature overnight. The reaction mixture was concentrated under reduced pressure, and the residue was purified by column chromatography on silica gel (hexane:ether=9:1) to give 3-acetoxyethyl-6-exo-t-butyldimethylsilyloxymethyl-7-endo-tetrahydropyranyloxybicyclo[3.3.0]oct-2-ene (XXI) (702 mg, 96%).

PMR(CDCl$_3$) δ: 0.07(s, 6H), 0.90(s, 9H), 2.00(s, 3H), 3.25–3.92(m, 5H), 4.12(t, J=7 Hz, 2H), 4.58(bs, 1H), 5.30(bs, 1H).

IRγ$_{max}^{CHCl_3}$ (cm$^{-1}$): 2950, 2850, 1730, 835.

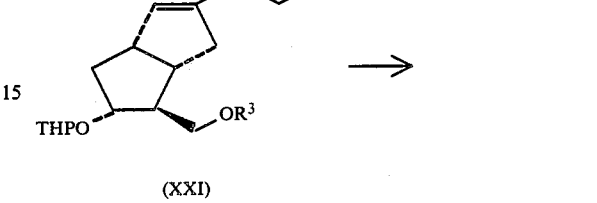

(XXI)

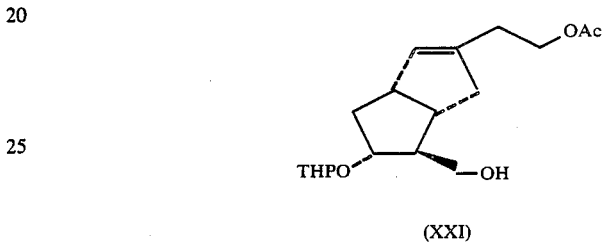

(XXI)

To a solution of said acetyl derivative (XXI) (702 mg, 1.60 mmol) in 5 ml of THF was added in an atmosphere of argon tetra-n-butylammonium fluoride (1M THF solution, 3.2 ml, 3.2 mmol). The mixture was stirred at room temperature for 3 hours, followed by addition of a saturated aqueous sodium chloride and removal of the THF by distillation under reduced pressre. The residual aqueous layer was extracted with ether, the extract was dried over sodium sulfate and the solvent was removed by distillation. The residue was purified by column chromatography on silica gel (hexane:ethyl acetate=1:1) to give 3-acetoxyethyl-6-exo-hydroxymethyl-7-endo-tetrahydropyranyloxybicyclo[3.3.0]oct-2-ene (XXII) (497 mg, 96%).

PMR(CDCl$_3$) δ: 2.03(s, 3H), 3.33–3.95(m, 5H), 4.13(t, J=7 Hz, 2H), 4.60(m, 1H), 5.33(bs, 1H).

IRγ$_{max}^{CHCl_3}$ (cm$^{-1}$): 3620, 3460, 1730, 835.

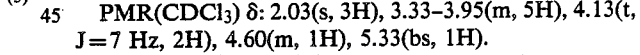

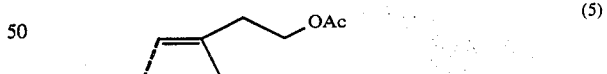

(XXII)

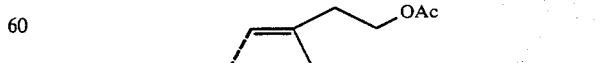

(XXIII)

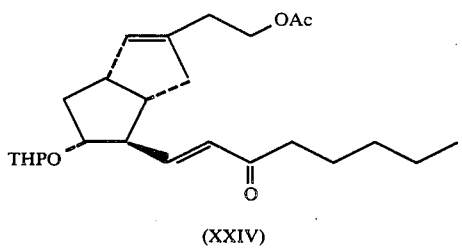

(XXIV)

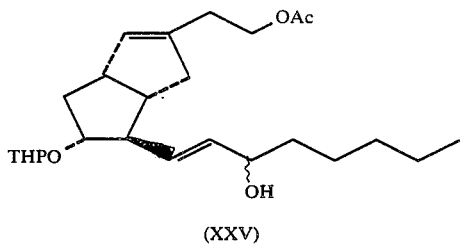

(XXV)

Collins reagent (CrO₃.2Py, 7.74 g, 30 mmol) and Celite (7.74 g) were suspended in an atmosphere of argon in methylene chloride (120 ml). To the suspension was added a methylenechloride solution (10 ml) of 3-acetoxyethyl-6-exo-hydroxymethyl-7-endo-tetrahydropyranyloxybicyclo[3.3.0]oct-2-ene (XXII) (497 mg, 1.53 mmol). The mixture was stirred at 0° C. for 30 min., followed by addition of sodium hydrogen sulfate monohydrate (13.36 g) and stirring at 0° C. for additional 10 min. The reaction mixture was filtered with the air of sodium sulfate and washed with methylene chloride. From the combined mixture of filtrate and washings was removed the solvent by distillation to give 3-acetoxyethyl-6-exo-formyl-7-endo-tetrahydropyranyloxybicyclo[3.3.0]oct-2-ene (XXIII).

Separately, sodium hydride (60% in oil, 120 mg, 3 mmol) was washed with n-hexane and suspended in 30 ml of DME(dimethoxyethane). To the suspension was added a DME solution (30 ml) of dimethyl (2-oxoheptyl)phosphonate (666 mg, 3 mmol), and the mixture was stirred at room temperature for 25 min. To the resulting mixture was added a DME solution (30 ml) of the 3-acetoxyethyl-6-exo-formyl-7-endo-tetrahydropyranyloxybicyclo[3.3.0]oct-2-ene (XXIV) obtained above followed by stirring at room temperature for 1 hour, then addition of a saturated aqueous solution of ammonium chloride, removal of the DME by distillation under reduced pressure and extraction with ether. The ether layer was washed with a saturated aqueous sodium chloride and dried over anhydrous sodium sulfate. The solvent was then removed by distillation, and the residue thus obtained was purified by column chromatography on silica gel (hexane:ethyl acetate=9:1) to give 3-acetoxyethyl-6-exo-(3-oxo-trans-1-octenyl)-7-endo-tetrahydropyranyloxybicyclo[3.3.0]oct-2-ene (XXVI) (275 mg, 43%).

PMR(CDCl₃) δ: 0.88(t, J=5 Hz, 3H), 2.02(s, 3H), 4.12(t, J=7 Hz, 2H), 4.55(m, 1H), 5.33(bs, 1H), 6.10(dd, J=16.2 Hz, 1H), 6.78(m, 1H).

IR$\gamma_{max}^{CHCl_3}$ (cm⁻¹): 2950, 2860, 1730, 1670, 1625.

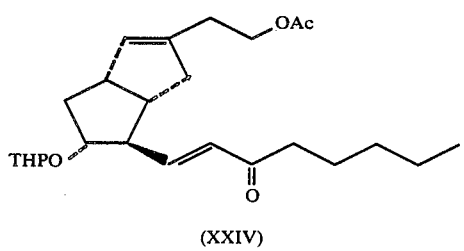

(XXIV)

To a solution of 3-acetoxyethyl-6-exo-(3-oxo-trans-1-octenyl)-7-endo-tetrahydropyranyloxybicyclo[3.3.-0]oct-2-ene (XXIV) (275 mg, 0.65 mmol) in methanol (40 ml) cooled to −20° C. was added sodium borohydride (226 mg, 6 mmol). The mixture was sitrred at −20° C. for 20 min., followed by addition of an excess of acetone, warming to room temperature, addition of a saturated aqueous solution of ammonium chloride and removal of the methanol and acetone by distillation under reduced pressure. The residual aqueous layer was extracted with ether and dried over anhydrous sodium sulfate. The solvent was then removed by distillation, and there was produced 3-acetoxyethyl-6-exo-(3-hydroxy-trans-1-octenyl)-7-endo-tetrahydropyranyloxybicyclo[3.3.9]oct-2-ene (XXV) (273 mg, 100%).

PMR(CDCl₃) δ: 0.90(t, J=5 Hz, 3H), 2.05(s, 3H), 4.15(t, J=7 Hz, 2H), 4.66(bs, 1H), 5.35(bs, 1H), 5.52(m, 2H).

IR$\gamma_{max}^{CHCl_3}$ (cm⁻¹): 3605, 3450, 2950, 2860, 1730.

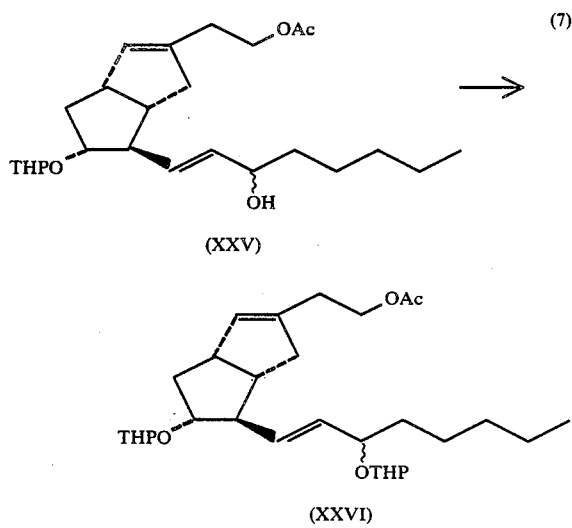

To a solution of 3-acetoxyethyl-6-exo-(3-hydroxy-trans-1-octenyl)-7-endo-tetrahydropyranyloxybicyclo[3.3.0]oct-2-ene (XXV) (273 mg, 0.65 mml) in methylene chloride (10 ml) were added in an atmosphere of argon dihydropyran (218 mg, 2.6 mmol) and phyridinium-p-toluenesulfonate (15 mg, 0.06 mmol). The mixture was stirred at room temperature for 4 hours, followed by dilution with ether, then successive washing with an aqueous solution of sodium hydrogen carbonate and a saturated aqueous sodium chloride, drying over sodium sulfate and then concentration under reduced pressure. The residue was purified by column chromatography of silica gel (hexane:ethyl acetate=10:1) to give 3-acetoxyethyl-6-exo-(3-tetrahydropyranyloxy-trans-1-octenyl)-

7-endo-tetrahydropyranyloxybicyclo[3.3.0]oct-2-ene (XXVI) (301 mg, 92%).

PMR(CDCl₃) δ: 0.87(t, J=5 Hz, 3H), 2.00(s, 3H), 4.12(t, J=7 Hz, 2H), 4.65(m, 2H), 5.35(bs, 1H), 4.52(m, 2H).

IR$\gamma_{max}^{CHCl3}$ (cm$^{-1}$): 2950, 2860, 1730.

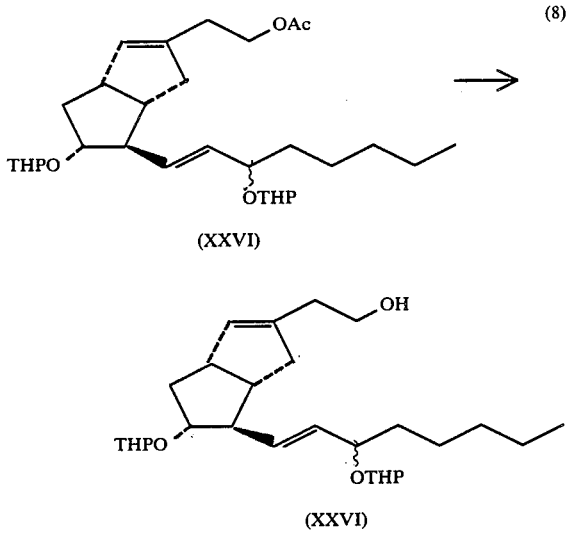

(XXVI)

(8)

(XXVI)

To a solution of 3-acetoxyethyl-6-exo-(3-tetrahydropyranyloxy-trans-1-octenyl)-7-endo-tetrahydropyranyloxybicyclo[3.3.0]oct-2-ene (XXVI) (301 mg, 0.59 mmol) in methanol (10 ml) was added anhydrous potassium carbonate (800 mg, 5.8 mmol). The mixture was stirred at room temperature for 1 hour, followed by addition of a saturated aqueous sodium chloride and removal of the methanol by distillation under reduced pressure. The residual aqueous layer was then extracted with ether. The ether layer was washed with a saturated aqueous soldium chloride, followed by drying over sodium sulfate and concentration under reduced pressure. The residue was purified by column chromatography on silica gel (hexane:ethyl acetate=9:1→4:1) to give 3-hydroxyethyl-6-exo-(3-tetrahydropyranyloxy-trans-1-octenyl)-7-endo-tetrahydropyrinyloxybicyclo[3.3.0]oct-2-ene (XXVII) (245 mg, 90%).

PMR(CDCl₃) δ: 0.88(t, J=5 Hz, 3H), 4.67(m, 2H), 5.42(m, 3H).

IR$\gamma_{max}^{CHCl3}$ (cm$^{-1}$) 3610, 3460, 2950, 2860.

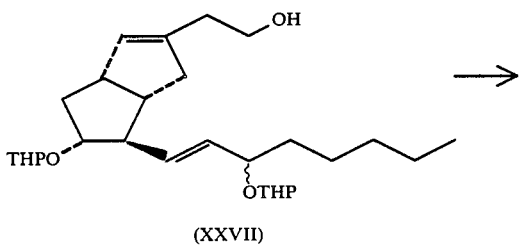

(XXVII)

(9)

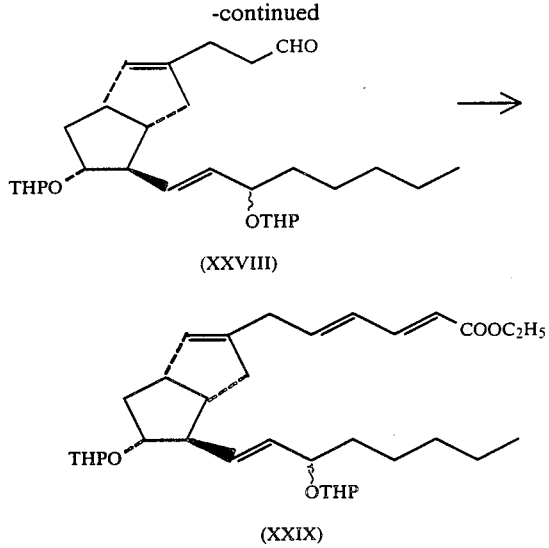

(XXVIII)

(XXIX)

Collins reagent (CrO₃.2Py, 2.6 g, 10.2 mmol) and Celite (2.6 g) were suspended in methylene chloride (40 ml). To the suspension was added a methylene chloride solution (5 ml) of 3-hydroxyethyl-6-exo-(3-tetrahydropyranyloxy-trans-1-octenyl)-7-endo-tetrahydropyranyloxybicyclo[3.3.0]oct-2-ene (XXVII) (245 mg, 0.53 mmol). The mixture was stirred at 0° C. for 30 min., followed by addition of sodium hydrogen sulfate monohydrate (5.2 g) and stirring for additional 10 min. The reaction mixture was filtered with the aid of sodium sulfate and washed with methylene chloride. From the combined mixture of filtrate and washings was removed the solvent by distillation, and there was obtained 3-formylmethyl-6-exo-(3-tetrahydropyranyloxy-trans-1-octenyl)-7-endo-tetrahydropyranyloxybicyclo[3.3.0]oct-2-ene (XXVIII).

Separately, sodium hydride (60% in oil, 40 mg, 1 mmol) was washed with n-hexane and suspended in 10 ml of DME. To the suspension was added triethyl-4-phosphonocrotonate (250 mg, 1 mmol), and the mixture was stirred at room temperature. To the resulting mixture was added a DME solution (5 ml) of the 3-formylmethyl-6-exo-(3-tetrahydropyranyloxy-trans-1-octenyl)-7-endo-tetrahydropyranyloxybicyclo[3.3.0]oct-2-ene (XXVIII) obtained above. The mixture was stirred at room temperature for 1 hour, followed by addition of a saturated aqueous solution of ammonium chloride, removal of the DME by distillation under reduced pressure and extraction with ether. The ether layer was washed with saturated aqueous sodium chloride and dried over anhydrous sodium sulfate. The solvent was then removed by distillation, and the residue thus obtained was purified by column chromatography on silica gel (hexane:ethyl acetate=9:1) to give 3-(5-ethoxycarbonyl-trans, trans-2,4-pentadienyl)-6-exo-(3-tetrahydropyranyloxy-trans-1-octenyl)-7-endo-tetrahydropyranyloxybicyclo[3.3.0]oct-2-ene (XXIX) (62 mg, 21%).

PMR(CDCl₃) δ: 0.92(t, J=5 Hz, 3H), 1.33(t, J=7 Hz, 3H), 2.92(m, 2H), 4.23(q, J=7 Hz, 2H), 4.72(m, 2H), 5.33(bs, 1H), 5.48(m, 2H), 5.77(d, J=15 Hz, 1H), 6.13(m, 2H), 7.20(m, 1H).

IR $\gamma_{max}^{CHCl3}$(cm$^{-1}$): 2950, 2860, 1700, 1640, 1619.

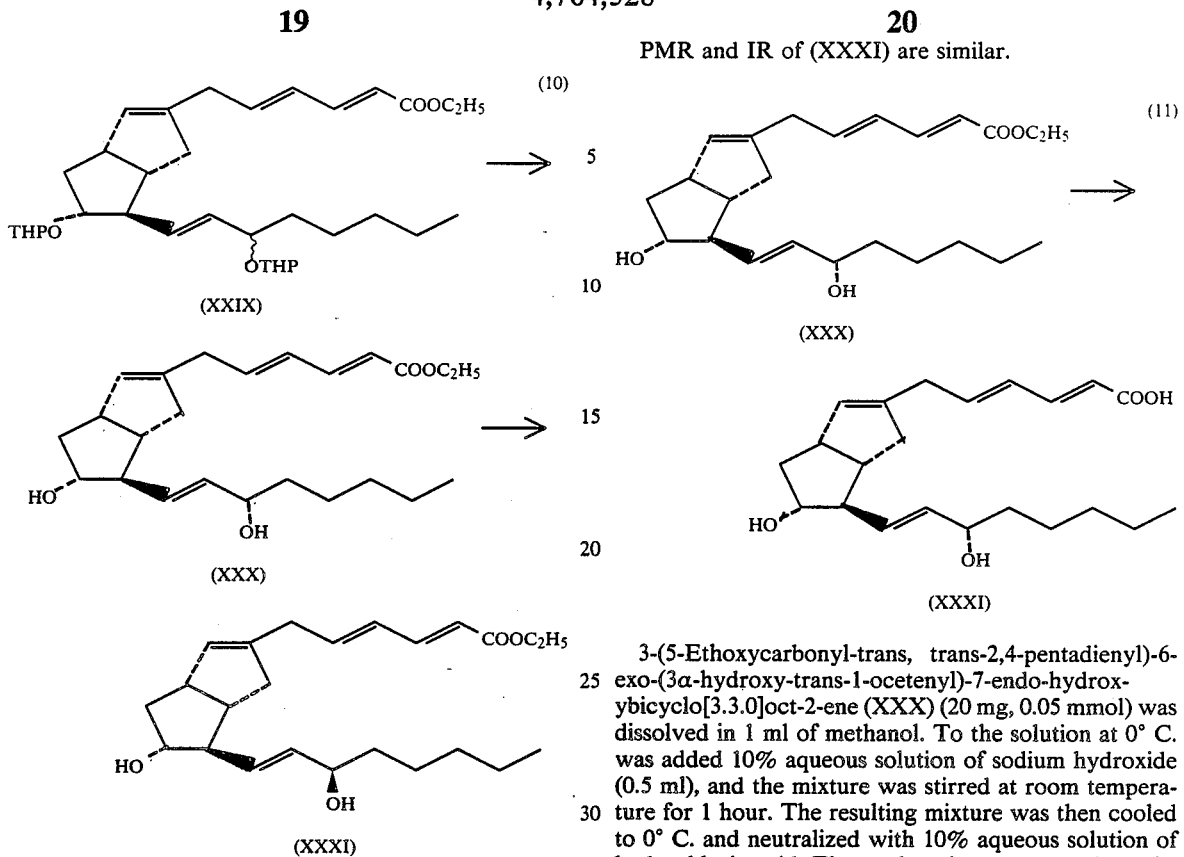

A solution of 3-(5-ethoxycarbonyl-trans, trans-2,4-pentadienyl)-6-exo-(3-tetrahydropyranyloxy-trans-1-ocetenyl)-7-endo-hydroxybicyclo[3.3.0]oct-2-ene (XXIX) (62 mg, 0.11 mmol) in a mixture of acetic acid water: THF (1 ml) (3:3:1 by volume) was stirred at 45°–50° C. for 24 hours. The reaction mixture was subjected to distillation under reduced pressure, and the residue was purified by column chromatography on silica gel (ether:methanol=40:1) to give 3-(5-ethoxycarbonyl-trans, trans-2,4-pentadienyl)-6-exo-(3α-hydroxy-trans-1-octenyl)-7-endo-hydroxybicyclo[3.3.0]oct-2-ene (XXX) (20 mg, 46%) as a more polar fraction and 3-(5-ethoxycarbonyl-trans, trans-2,4-pentadienyl)-6-exo-(3β-hydroxy-trans-1-ocetenyl)-7-endo-tetrahydropyranyloxybicyclo[3.3.0]oct-2-ene (XXXI) (12 mg, 28%) as a less polar fraction.

(XXX)

PMR (CDCl$_3$) δ: 0.87(t, J=5 Hz, 3H), 1.27(t, J=7 Hz, 3H), 2.85(m, 2H), 4 15(q, J=7 Hz, 2H), 5.27(bs, 1H), 5.47(m, 2H), 5.70(d, J=15 Hz, 1H), 6.03 (m, 2H), 7.20(m, 1H).

IR $\gamma_{max}^{CHCL3}$(cm$^{-1}$): 3600, 3400, 2960, 2870, 1700, 1640, 1620.

PMR and IR of (XXXI) are similar.

3-(5-Ethoxycarbonyl-trans, trans-2,4-pentadienyl)-6-exo-(3α-hydroxy-trans-1-ocetenyl)-7-endo-hydroxybicyclo[3.3.0]oct-2-ene (XXX) (20 mg, 0.05 mmol) was dissolved in 1 ml of methanol. To the solution at 0° C. was added 10% aqueous solution of sodium hydroxide (0.5 ml), and the mixture was stirred at room temperature for 1 hour. The resulting mixture was then cooled to 0° C. and neutralized with 10% aqueous solution of hydrochloric acid. The methanol was removed by distillation under reduced pressure, and the residue was extracted with ethyl acetate. The organic layer was washed with saturated aqueous sodium chloride and dried over sodium sulfate. The solvent was then removed by distillation, and there was obtained 3-(5-carboxy-trans, trans-2,4-pentadienyl)-6-exo-(3α-hydroxy-trans-1-octenyl)-7-endo-hydroxybicyclo[3.3.0]oct-2-ene (XXXII) (18 mg, 100%).

PMR(d$_6$-acetone) δ: 0.82 (t, J=5H, 3H), 2.90(m, 2H), 5.25(bs, 1H), 5.42(m, 2H), 5.70(d, J=15 Hz, 1H), 6.10(m, 2H), 7.20(m, 1H).

IR $\gamma_{max}^{CHCl3}$(cm$^{-1}$): 3400, 2960, 2860, 1690, 1610.

EXAMPLES 7-10

Condensation reaction with a variety of dimethyl(2-oxoalkyl)phosphonates, reductions with sodium borohydride, introduction reactions of a protective group, deacetylation reactions, oxidation reactions, condensation reactions with triethyl-4-phosphonocrotonate and deprotection reactions yielded the pentadienoic acid derivatives shown in Table 3. In every case, the more polar isomer was designated as α-epimer, and the less polar isomer as β-epimer. The spectrum data are shown in Table 4.

TABLE 3

| Ex. No. | Starting phosphonate | R in the product (I) |
|---|---|---|
| 7 | (MeO)$_2$P(=O)—CH$_2$—C(=O)—CH(CH$_3$)—(CH$_2$)$_3$CH$_3$ | |
| 8 | (MeO)$_2$—P(=O)—CH$_2$—C(=O)—C(CH$_3$)$_2$—(CH$_2$)$_3$CH$_3$ | |

TABLE 3-continued

| Ex. No. | Starting phosphonate | R in the product (I) |
|---|---|---|
| 9 | (MeO)$_2$—P(=O)—CH$_2$—C(=O)—CH(CH$_2$—CH$_2$)(CH$_2$—CH$_2$)  [cyclopentyl-CH<] | cyclopentyl |
| 10 | (MeO)$_2$—P(=O)—CH$_2$—C(=O)—CH$_2$—CH(CH$_3$)—CH$_2$—CH$_2$—CH=C(CH$_3$)$_2$ | (CH$_3$)CH-CH$_2$CH$_2$-CH=C(CH$_3$)$_2$ |

TABLE 4

| Ex. No. | R in the product (I) | $\nu_{OH}$ | IR (cm$^{-1}$) $\nu_{C=O}$ | $\nu_{C=C}$ |
|---|---|---|---|---|
| 7 | (branched pentyl) | 3400 | 1690 | 1610 |
| 8 | (branched pentyl) | 3400 | 1690 | 1613 |
| 9 | (cyclopentyl) | 3400 | 1690 | 1610 |
| 10 | (geranyl-type) | 3400 | 1690 | 1612 |

TEST EXAMPLE

Platelet Aggregation-Inhibitory Activities

Using a syringe containing 3.8% sodium citrate solution (1 volume), 9 volumes of blood is drawn from the carotid artery of a rabbit. Said blood is centrifuged to give platelet-rich plasma (PRP: $7 \times 10^5/\mu l$).

In a cuvette is placed 250 ul of said PRP, followed by incubation in a thermostat at 37° C. for 2 min. Then, 20 μl of physiological saline buffer solution of a 2,4-pentadienoic acid derivative to be tested is added, and the mixture is incubated for 3 min. A platelet-aggregation inducer, an arachidonic acid solution, a collagen solution or an ADP solution is then added, and platelet aggregation is measured by the Born's turbimetry (which is described, for example, in Journal of Physiology, vol. 168, p. 178 (1968)). 50% Inhibitory concentration of the platelet aggregation caused by arachidonic acid (60 μmol), collagen (10 μg/ml) or ADP (5 μmol) is shown in Table 5 in comparison with prostaglandin I$_2$, aspirin or dipyridamol.

As shown in Table 5 with reference to typical examples, the α-epimers showed a marked platelet antiaggregation activity. It was demonstrated that 2,4-pentadienoic acid derivatives of the invention not shown in Table 5 also had a similar antiaggregation activity. 50% Inhibitory concentration as indicated in Table 5 means the concentration of a 2,4-pentadienoic acid derivative needed for inhibiting the platelet aggregation by 50% by the introduction of said 2,4-pentadienoic acid derivative, taking the platelet aggregation in the absence of 2,4-pentadienoic acid derivatives of the invention as 100%.

TABLE 5

| Structural formula | Ex. No. | Antiplatelet activity 50% Inhibitory concentration (mol) | | |
|---|---|---|---|---|
| | | Arachidonic acid | Collagen | ADP |
| (bicyclic structure with COOH, HO, OH, pentyl chain) | 1 | $4.7 \times 10^{-7}$ | $3.2 \times 10^{-7}$ | $5.2 \times 10^{-7}$ |
| (bicyclic structure with COOH, HO, OH, cyclopentyl) | 4 | $2.9 \times 10^{-7}$ | $2.3 \times 10^{-7}$ | $3.9 \times 10^{-7}$ |
| (bicyclic structure with COOH, HO, OH, pentyl chain) | 6 | $8.2 \times 10^{-7}$ | $5.0 \times 10^{-7}$ | $7.0 \times 10^{-7}$ |

TABLE 5-continued

| | | Antiplatelet activity | | |
| | | 50% Inhibitory concentration (mol) | | |
| Structural formula | Ex. No. | Arachidonic acid | Collagen | ADP |
|---|---|---|---|---|
| (structure) | 9 | $1.8 \times 10^{-6}$ | $1.1 \times 10^{-6}$ | $1.4 \times 10^{-6}$ |
| PGI₂ (structure) | Control | $2.5 \times 10^{-7}$ | $2.2 \times 10^{-7}$ | $3.8 \times 10^{-7}$ |
| Aspirin (structure) | Control | $1.7 \times 10^{-5}$ | $2.0 \times 10^{-4}$ | $\geq 1 \times 10^{-3}$ |
| (structure) | Control | $\geq 1 \times 10^{-3}$ | $\geq 1 \times 10^{-3}$ | $4.7 \times 10^{-4}$ |

ACUTE TOXICITY

An acute toxicity test was run in ICR male mice (5-week old) by intraperitoneal administration. LD$_{50}$s' of the compounds of the invention were 2 mg/kg or higher in every case thereby demonstrating high safety as compared with the effective dose.

According to the present invention, there are provided novel 2,4-pentadienoic acid derivatives and platelet-aggregation inhibitors containing the same.

The above-mentioned compounds of the invention remarkably inhibit the platelet aggregation induced by arachidonic acid, collagen or ADP and are useful as a prophylactic agent for diseases caused by platelet aggregation, particularly thrombosis in which platelet aggregation participates such as myocardial infarction, ischemic attacks after cerebral blooding and cerebral thrombosis As platelet aggregation participates in metastasis of cancers, the above-mentioned compounds of the invention can also be used as a prophylactic agent for metastasis of cancers.

What is claimed is:

1. A 2,4-pentadienoic acid derivative represented by the formula (I)

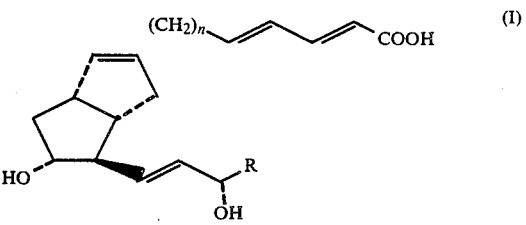

wherein R is a group having the formula

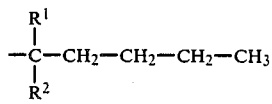

in which $R^1$ and $R^2$ may be the same or different and represent a hydrogen atom or a lower alkyl group, a group having the formula

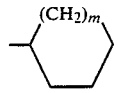

in which m represents 1 or 2 or a group having the formula

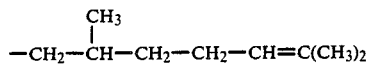

and n represents an integer from 0 to 3 or a lower alkyl, lower alkoxymethyl, lower aliphatic acyloxymethyl or benzyl ester thereof or a pharmacologically acceptable salt thereof.

2. A platelet aggregation inhibitory pharmaceutical composition comprising a therapeutically effective amount to inhibit platelet aggregation of a 2,4-pentadienoic acid derivative or an ester or a pharmacologically acceptable salt thereof according to claim 1 and a pharmaceutical carrier therefor.

3. The platelet aggregation inhibitory pharamaceutical composition according to claim 2, which is a thrombosis-prophylactic agent.

4. A method for inhibiting platelet aggregation which comprises administering to mammary animals an effective amount to inhibit platelet aggregation of a 2,4-pentadienoic acid derivative or an ester or a pharmacologically acceptable salt thereof according to claim 1.

5. A method for treating arterial thrombosis of the extremities or cerebral thrombosis, said method comprising administering to a mammary animal in need of such treatment an effective amount to inhibit platelet aggregation of a 2,4-pentadienoic acid derivative or ester or pharmaceutically acceptable salt thereof according to claim 1.

* * * * *

UNITED STATES PATENT AND TRADEMARK OFFICE
CERTIFICATE OF CORRECTION

PATENT NO. : 4,764,528

DATED : August 16, 1988

INVENTOR(S) : Keiko Chiba, Makoto Takai, and Toshio Wakabayashi

It is certified that error appears in the above-identified patent and that said Letters Patent is hereby corrected as shown below:

In the Abstract, line 6, change "hydroxytrans-1-octenyl)-7-endo-hydroxybicyclo[3.3.-" to --hydroxy-trans-1-octenyl)-7-endo-hydroxybicyclo[3.3.- --.

Column 1, line 21, change "group" to --groups--.

Column 2, line 67, change "fornula" to --formula--.

Column 5, line 14, change "représents" to --represents--.

Column 5, line 35, change "given" to --give--.

Column 6, lines 30-40, the formula should appear as follows:

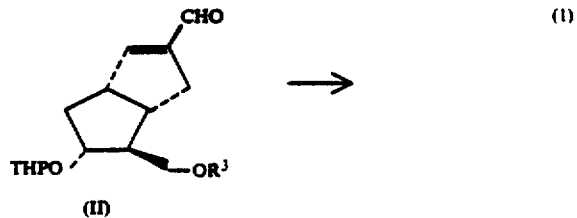

UNITED STATES PATENT AND TRADEMARK OFFICE
CERTIFICATE OF CORRECTION

PATENT NO. : 4,764,528

DATED : August 16, 1988

INVENTOR(S) : Keiko Chiba, Makoto Takai, and Toshio Wakabayashi

It is certified that error appears in the above-identified patent and that said Letters Patent is hereby corrected as shown below:

Column 7, lines 60-67, the formula should appear as follows:

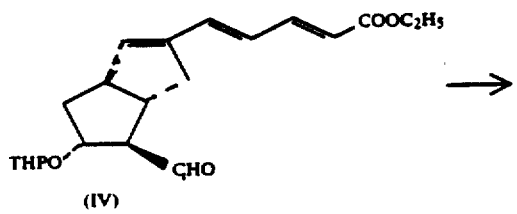

Column 8, line 25, change "thé" to --the--.

Column 9, lines 1-9, the formula should appear as follows:

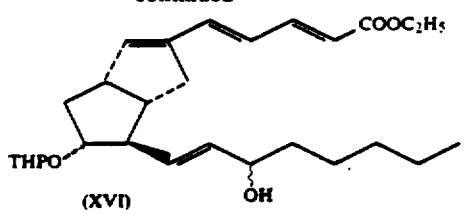

Column 9, line 5 after the formula, change "in" to --to--.

UNITED STATES PATENT AND TRADEMARK OFFICE
CERTIFICATE OF CORRECTION

PATENT NO. : 4,764,528

DATED : August 16, 1988

INVENTOR(S) : Keiko Chiba, Makoto Takai, and Toshio Wakabayashi

It is certified that error appears in the above-identified patent and that said Letters Patent is hereby corrected as shown below:

Column 11, TABLE 1, Ex. No. 5, the formula should appear as follows:

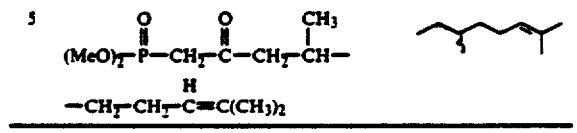

Column 11, TABLE 2, Ex. No. 2, the formula should appear as follows:

Column 13, lines 1-10, the formula should appear as follows:

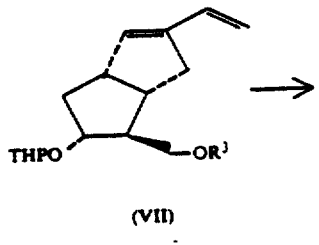

(VII)

UNITED STATES PATENT AND TRADEMARK OFFICE
CERTIFICATE OF CORRECTION

PATENT NO. : 4,764,528
DATED : August 16, 1988
INVENTOR(S) : Keiko Chiba, Makoto Takai, and Toshio Wakabayashi It is certified that error appears in the above-identified patent and that said Letters Patent is hereby corrected as shown below:

Column 13, line 27, change "(13 5 ml)" to --(13.5 ml)--.

Column 13, line 34, change "sulfate The" to --sulfate. The--.
Column 13, line 64, "567" to -- 657 --.
Column 13, line 66, change "achydride" to --anhydride--.

Column 14, lines 20-29, the formula should appear as follows:

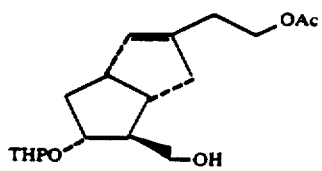

(XXI)

Column 14, line 36, change "pressre" to --pressure--.

Column 15, line 23, change "air" to --aid--.

Column 16, line 57, change "mml)" to --mmol)--.

Column 16, line 59, change "phyridini-" to --pyridini- --.

Column 19, line 51, change "4 15" to --4.15--.

Column 19, line 54, change "CHCL" to --CHCl--.

UNITED STATES PATENT AND TRADEMARK OFFICE
CERTIFICATE OF CORRECTION

PATENT NO. : 4,764,528

DATED : August 16, 1988

INVENTOR(S) : Keiko Chiba, Makoto Takai, and Toshio Wakabayashi

It is certified that error appears in the above-identified patent and that said Letters Patent is hereby corrected as shown below:

Columns 19 and 20, TABLE 3, Ex. No. 7, the formula should appear as follows:

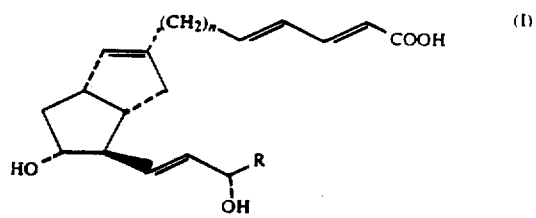

Column 24, lines 45-57, the formula should appear as follows:

Signed and Sealed this

Fourteenth Day of March, 1989

Attest:

DONALD J. QUIGG

Attesting Officer     Commissioner of Patents and Trademarks